(12) United States Patent
Morganstern et al.

(10) Patent No.: US 11,642,274 B2
(45) Date of Patent: *May 9, 2023

(54) METHOD FOR TREATING ORGANIC ERECTILE DYSFUNCTION

(71) Applicant: BMR MEDICAL LLC, Marietta, GA (US)

(72) Inventors: Steven Morganstern, Sandy Springs, GA (US); Carlos Becerra, Atlanta, GA (US)

(73) Assignee: BMR Medical LLC, Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/216,895

(22) Filed: Mar. 30, 2021

(65) Prior Publication Data

US 2021/0212882 A1 Jul. 15, 2021

Related U.S. Application Data

(63) Continuation of application No. 16/266,293, filed on Feb. 4, 2019, now Pat. No. 10,987,273, which is a
(Continued)

(51) Int. Cl.
*A61H 9/00* (2006.01)
*A61H 23/00* (2006.01)
(Continued)

(52) U.S. Cl.
CPC ............. *A61H 9/0092* (2013.01); *A61F 5/41* (2013.01); *A61H 23/008* (2013.01); *A61F 2005/414* (2013.01); *A61F 2005/415* (2013.01); *A61H 2201/0103* (2013.01); *A61H 2201/10* (2013.01); *A61H 2205/086* (2013.01); *A61H 2205/087* (2013.01); *A61H 2205/106* (2013.01); *A61H 2205/108* (2013.01); *A61H 2230/045* (2013.01); *A61M 2005/006* (2013.01); *A61M 2202/0225* (2013.01)

(58) Field of Classification Search
CPC .......... A61F 2/26; A61M 5/20; A61M 13/003
USPC .............................................. 600/38, 39, 41
See application file for complete search history.

(56) References Cited

U.S. PATENT DOCUMENTS 4,127,118 A 11/1978 Latorre
5,554,103 A 9/1996 Zheng et al.
(Continued)

OTHER PUBLICATIONS

Anti-Aging Medical Systems: "Carboxy Pen"; believed to have published on Apr. 24, 2013.
(Continued)

*Primary Examiner* — Samuel G Gilbert
(74) *Attorney, Agent, or Firm* — Barnes & Thornburg LLP; Jeffrey R. Stone

(57) ABSTRACT

In a method of treating erectile dysfunction in a patient, a predetermined course of external counter-pulsation treatment is applied to a lower body portion of the patient. After the predetermined course of external counter-pulsation treatment is applied, a predetermined course of low intensity shockwave treatment is applied to a penile area of the patient. After the course of low intensity shockwave treatment, a predetermined course of carboxy therapy is applied to a corpora cavernosa of the patient.

9 Claims, 1 Drawing Sheet

Related U.S. Application Data continuation of application No. 15/064,162, filed on Mar. 8, 2016, now Pat. No. 10,195,103.

(51) Int. Cl.
*A61F 5/41* (2006.01)
*A61M 5/00* (2006.01)

(56) References Cited

U.S. PATENT DOCUMENTS

| | | | |
|---|---|---|---|
| 5,997,540 | A | 12/1999 | Zheng et al. |
| 6,251,076 | B1 | 6/2001 | Hovland et al. |
| 6,572,621 | B1 | 6/2003 | Zheng et al. |
| 6,589,267 | B1 | 7/2003 | Hui |
| 6,620,116 | B2 | 9/2003 | Lewis |
| 6,858,012 | B2 | 2/2005 | Burns et al. |
| 6,863,670 | B2 | 3/2005 | Zheng et al. |
| 6,962,599 | B2 | 11/2005 | Hui |
| 7,048,702 | B2 | 5/2006 | Hui |
| 7,314,478 | B2 | 1/2008 | Hui |
| 7,517,312 | B2 | 4/2009 | Loeb et al. |
| 7,713,211 | B2 | 5/2010 | Anderson et al. |
| 7,891,066 | B2 | 7/2011 | Lewis |
| 9,132,245 | B2 | 9/2015 | Mantell |
| 10,195,103 | B2 * | 2/2019 | Morganstern ........ A61H 23/008 |
| 10,987,273 | B2 * | 4/2021 | Morganstern ............. A61F 5/41 |
| 2015/0073312 | A1 | 3/2015 | Ein-Gal |
| 2017/0143490 | A1 | 5/2017 | Forsell |

OTHER PUBLICATIONS www.bodyrenewal.co.za: "Carboxytherapy for Sexual Rejuvenation / Erectile Dysfunction"; Sep. 9, 2015.

Froschemaier et al.: "Enhanced External Counterpulsation as a New Treatment Modality for Patients with Erectile Dysfunction"; Urologia Internationals; Jul. 20, 1998.

Gruenwald et al.: "Shockwave treatment of erectile dysfunction"; https://beta.openaire.eu/search/publication?articleId=od; 2013.

Hind et al.: "Initial results of treatment with Linear Shockwave Therapy (LSWT) by Renova in patients with Erectile Dysfunction"; believed to have been published Aug. 30, 2013.

Fabrizio et al.,"Experience fo Carboxytherapy in Conservative Treatment of Peyronie's disease"; XXI Congresso Nazionale Roma, Associazione Urologi Italiani; 2012.

Reisman et al.: "Initial experience with linear focused shockwave treatment for erectile dysfunction: a 6-month follow-up pilot study"; International Journal of Impotence Research (2014), 1-5; Oct. 18, 2014.

Stein: "Endothelial Dysfunction, Erectile Dysfunction, and Coronary Heart Disease: The Pathophysiologic and Clinical Linkage", Reviews in Urology; 2003.

* cited by examiner

METHOD FOR TREATING ORGANIC ERECTILE DYSFUNCTION

CROSS-REFERENCE TO RELATED APPLICATIONS

This application is a continuation of U.S. application Ser. No. 16/266,293, filed Feb. 4, 2019 and entitled METHOD FOR TREATING ORGANIC ERECTILE DYSFUNCTION and is a continuation of U.S. application Ser. No. 15/064,162, filed Mar. 8, 2016, issued as U.S. Pat. No. 10,195,103, dated Feb. 5, 2019 and entitled METHOD FOR TREATING ORGANIC ERECTILE DYSFUNCTION, the entire contents of which are incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates to treatment methods and, more specifically, to a method for treating erectile dysfunction.

2. Description of the Related Art

Erectile dysfunction (ED) is a condition in which the patient is unable to achieve or sustain an erection suitable for sexual intercourse. Physical causes for ED include illness, medications, injury and poor blood flow to the corpora cavernosa of the patient's penis.

Treatments for ED include medications and physical treatments designed to increase blood flow to the corpora cavernosa. Medical treatments include phosphodiesterase type 5 (PDE5) inhibitors, such as sildenafil, tadalafil and vardenafil. These medications tend to stimulate generation of cyclic guanosine monophosphate (cGMP) in smooth muscle cells, thereby relaxing the smooth muscle, which increases blood flow to the corpora cavernosa.

Non-invasive physical treatments include external counter-pulsation (ECP) therapy to the legs of the patient. ECP involves applying pneumatic cuffs to the patient's thighs and buttocks and monitoring the patient's heart rate and rhythm. The cuffs inflate and deflate based on the patient's heart rhythm, in which the cuffs inflate at the beginning of diastole and deflate at the beginning of systole. Typically, the cuffs are inflated to about 200-300 mmHg. This generally increases overall cardiac output, which increases blood flow to the corpora cavernosa. However, this treatment is effective for only a limited number of patients.

Another physical treatment includes applying low intensity shock waves to the patient's penile area. These treatments are designed to stimulate tissue to promote the growth of smaller blood vessel around the corpora cavernosa. However, use of this treatment by itself has had limited effectiveness.

While medical treatments can be effective for certain patients, the medications can interact with other drugs and can have undesirable side effects. Physical treatments tend to have limited effectiveness.

Therefore, there is a need for effective non-medical treatment of erectile dysfunction.

SUMMARY OF THE INVENTION

The disadvantages of the prior art are overcome by the present invention which, in one aspect, is a method of treating erectile dysfunction in a patient, in which a predetermined course of external counter-pulsation treatment is applied to a lower body portion of the patient. After the predetermined course of external counter-pulsation treatment is applied, a predetermined course of low intensity shockwave treatment is applied to a penile area of the patient. After the course of low intensity shockwave treatment, a predetermined course of carboxy therapy is applied to a corpora cavernosa of the patient.

In another aspect, the invention is an erectile dysfunction treatment method, in which major blood vessel flow is increased with external counter-pulsation treatment to a lower body portion of a patient by applying external counter-pulsation treatments to the patient for a predetermined number of days per week for a predetermined number of weeks. The predetermined course of external counter-pulsation treatments comprises the steps of: sensing an electrocardiogram (ECG) of the patient; applying an inflatable cuff to at least one of a calf, a lower thigh, an upper thigh and buttocks of the patient; applying a plurality of counter-pulsations to the cuff; during a diastole sensed by the ECG, inflating the cuff to a predetermined pressure; and (v) during onset of a systole sensed by the ECG, rapidly releasing pressure from the cuff. Blood vessel growth is stimulated in a penile area of the patient with low intensity shockwave treatment of the penile area of the patient by performing a plurality of treatments that each include applying shock waves having a maximum energy of 0.09 mjmm2 to the penile area at a predetermined rate for a predetermined amount of time per treatment, wherein plurality of treatments include one treatment per day for two to three days per week over a course of five weeks and wherein the predetermined rate is about 300 pulses per minute and wherein the predetermined amount of time per treatment is within a range of between 10 minutes and 20 minutes. After the external counter-pulsation treatment and after the low intensity shockwave treatment, pliability of a corpora cavernosa of the patient is increased with carboxy treatment by injecting about 160 cc of carbon dioxide into the corpora cavernosa at four different sites along the shaft of patient's penis twice per week, but 48 hours apart, for twelve consecutive weeks.

In yet another aspect, the invention is a treatment method for treating erectile dysfunction treatment in a patient, in which a predetermined amount of carbon dioxide is injected into the corpora cavernosa of the patent.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
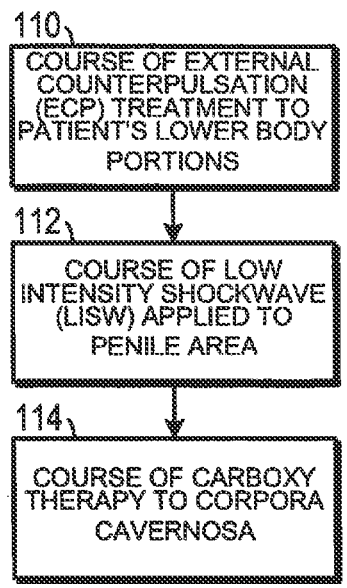
FIG. 1 is a flow chart showing one embodiment of a method of treating ED.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an." and "the" includes plural reference, the meaning of "in" includes "in" and "on." As used herein "carboxy therapy" means injecting carbon dioxide into the patient's corpora cavernosa.

As shown in FIG. 1, in one embodiment of a treatment method for ED, a course of external counter-pulsation (ECP) is applied to the lower body portions of the patient 110. A course of low intensity shockwave (LISW) therapy is applied to the patient's penile area 112. Next, carboxy therapy is applied to the patient's corpora cavernosa 114.

The course of external counter-pulsation treatment includes applying external counter-pulsation treatments to the patient for a predetermined number of days per week for a predetermined number of weeks. In the low intensity shockwave treatment (LISW), shock waves having a maximum energy of 0.09 mJmm2 are applied with a local applicator to the penile area once per day for two or three days per week over a course of five weeks. U.S. Publication No. US-2015/0073312-A1, filed by Ein-Gal, discloses one method of low intensity shockwave treatment and is incorporated herein by reference for the purpose of disclosing low intensity shockwave treatment. In a typical treatment, about 300 pulses are applied per minute over the course of between 10 minutes and 20 minutes. The LISW treatment stimulates neovascularization and improves penile blood flow and endothelial function when applied to the corpora cavernosa.

In applying the course of external counter-pulsation treatments an electrocardiogram (ECG) sensing device is applied to the patient and the ECG is sensed. U.S. Pat. Nos. 7,314,478 and 7,314,478, both issued to Hui, disclose a counter-pulsation apparatus and method for controlling the apparatus and is incorporated herein by reference for the purpose of disclosing counter-pulsation methods. An inflatable cuff is applied to at least one of the patient's calf, lower thigh, upper thigh or buttocks. Typically, cuffs are applied to both of the lower thighs and to both of the upper thighs. Counter pulsations are applied to the cuffs by inflating the cuffs to a pressure of about 300 mm Hg during a diastole sensed by the ECG. Pressure is then rapidly released from the cuffs during onset of the systole, as sensed by the ECG. Counter-pulsations are performed repeatedly during a treatment sessions that last about one hour, which are performed five days per week over a course of four weeks.

Circulatory blood flow velocity in the patient is tested both before and after the ECP treatment, typically with a duplex Doppler. U.S. Pat. No. 6,251,076, issued to Hovland et al., discloses one method of determining blood flow velocity in a penile artery and is incorporated herein by reference for the purpose of disclosing methods of determining blood flow velocity. The ECP treatment is repeated until it achieves a predetermined resultant increase in blood flow, (While the threshold necessary to move past ECP treatments is a matter of the individual treating physician's judgment, it is typically a doubling in blood flow through the major blood vessels near the groin.) (Also, it should be noted that the term "ECP" is sometimes confused with "EECP," which is a registered a trademark for a brand of ECP. However, the EECP brand can be employed as the type of ECP used.)

Figure 2:
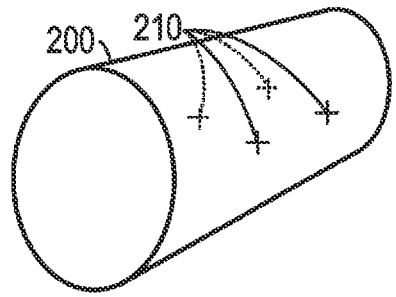
FIG. 2 is a schematic diagram showing carbon dioxide injection sites.
Figure 3:
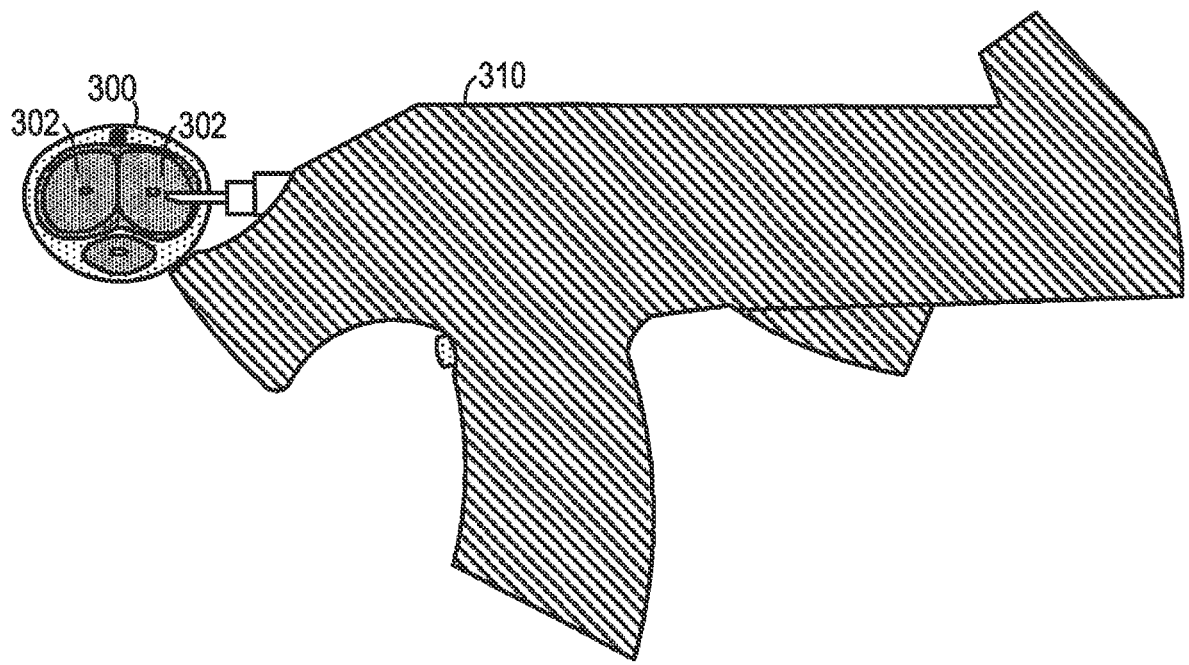
FIG. 3 is a schematic diagram showing carbon dioxide injection into a corpus cavemosum.

As shown in FIG. 2, in the carboxy therapy, about 160 cc of carbon dioxide is injected into the corpora cavernosa of the patient, typically at four different sites 210 along the patient's penile shaft 200. U.S. Pat. No. 9,132,245, issued to Mantell, discloses a carboxy therapy application and is incorporated here by reference to disclose one device and method for administering carboxy therapy. The injections are performed with a micro-injection carboxy therapy applicator 310, as shown in FIG. 3, that injects the carbon dioxide into each corpus cavemosum 302 in the patient's penis 300. This is typically performed twice per week, but about 48 hours apart, for twelve consecutive weeks. The carboxy therapy infuses carbon dioxide into the tissues, causing the body to interpret the presence of the carbon dioxide as an oxygen deficiency, which results in the production of vascular endothelial growth factors in the tissues. This encourages vascular growth and local reduction in fat tissue, which results in increased blood flow to the corpora cavernosa. It is important to begin the carboxy therapy after the ECP and the LISW treatments, which could cause the carbon dioxide to disperse at an undesirable rate and, thereby reduce its effectiveness.

One embodiment treats ED with the carboxy therapy disclosed above and without the LISW and ECP treatments. It has been found that injecting carbon dioxide directly into the corpora cavernosa can have a substantial effect by itself. Similarly, in some cases, only carboxy treatment to the corpora cavernosa without both, or either, LISW or ECP treatment may be used to treat ED.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A method for increasing blood flow in a patient's penis and for treating erectile dysfunction, comprising:
   (a) increasing blood flow in the penis by applying a predetermined course of external counter-pulsation treatment to a lower body portion of the patient;
   (b) stimulating blood vessel growth in the patient's penis by applying a predetermined course of shock wave therapy to the patient's penis,
      wherein the predetermined course of carboxy therapy to the at least one corpora cavernosum is configured to produce vascular endothelial growth factors in tissues of the patient's penis, and
      wherein the predetermined course of carboxy therapy to the at least one corpora cavernosum is further configured to reduce fat tissue within the patient's penis; and
   (c) increasing pliability of at least one corpora cavernosum within the patient's penis by applying a predetermined course of carboxy therapy to the at least one corpora cavernosum.

2. The method of claim 1, further comprising injecting a predetermined amount of carbon dioxide into the at least one corpora cavernosum.

3. The method of claim 1, further comprising:
after applying the predetermined course of external counter-pulsation treatment, and
before applying the predetermined course of shock wave therapy, testing blood flow velocity in a penile artery of the patient.

4. The method of claim 1, wherein the predetermined course of shock wave therapy comprises:
performing one or more treatments that each include applying shock waves having a maximum energy of 0.09 mJmm$^2$ to the patient's penis at a predetermined rate for a predetermined amount of time per treatment.

5. The method of claim 1, further comprising:
before applying the predetermined course of external counter-pulsation treatment, testing blood flow velocity in a penile artery of the patient.

6. The method of claim 5, comprising:
after applying the predetermined course of external counter-pulsation treatment, and
before applying the predetermined course of shock wave therapy, testing blood flow velocity in the penile artery of the patient.

7. The method of claim 6, further comprising:
comparing the blood flow velocity tested before applying the predetermined course of external counter-pulsation treatment with the blood flow velocity tested after applying the predetermined course of external counter-pulsation treatment, and before applying the predetermined course of shock wave therapy, to determine an increase in blood flow as a result of applying the predetermined counter-pulsation treatment; and
comparing the determined increase in blood flow with a predetermined increase in blood flow.

8. The method of claim 7, further comprising:
determining that the determined increase in blood flow is less than the predetermined increase in blood flow; and
repeating the course of external counter-pulsation treatment until the blood flow increase is determined to achieve the predetermined increase in blood flow.

9. The method of claim 8, further comprising:
determining that the determined increase in blood flow achieved the predetermined increase in blood flow; and
applying the predetermined course of shock wave therapy.

* * * * *